(12) United States Patent
Wang (10) Patent No.: US 6,759,416 B2
(45) Date of Patent: Jul. 6, 2004

(54) ANTICANCER CONJUGATES OF CAMPTOTHECIN AND UNSATURATED FATTY ACIDS

(75) Inventor: Yuqiang Wang, Cupertino, CA (US)

(73) Assignee: Panorama Research, Inc., Mountain View, CA (US)

( * ) Notice: Subject to any disclaimer, the term of this patent is extended or adjusted under 35 U.S.C. 154(b) by 0 days.

(21) Appl. No.: 10/457,501

(22) Filed: Jun. 9, 2003

(65) Prior Publication Data

US 2004/0034033 A1 Feb. 19, 2004

Related U.S. Application Data

(60) Provisional application No. 60/444,392, filed on Feb. 3, 2003, and provisional application No. 60/401,195, filed on Aug. 6, 2002.

(51) Int. Cl.⁷ .................. C07D 471/00; A61K 31/44
(52) U.S. Cl. .................................... 514/283; 546/48
(58) Field of Search ........................... 546/48; 514/283

(56) References Cited

PUBLICATIONS

Lundberg (Anti–Cancer Drug Design (1998), 13(5), 453–461). Abstract.*

* cited by examiner

*Primary Examiner*—Bruck Kifle
(74) *Attorney, Agent, or Firm*—Greenberg Traurig, LLP; Michel Morency; James F. Ewing (57) ABSTRACT

The present invention provides novel conjugates of camptothecin compounds and long-chain unsaturated fatty acid. The novel conjugates can be used to treat mammalian cell proliferative diseases such as cancer.

11 Claims, 3 Drawing Sheets

Fig. 1. Synthesis of compound 6

FIG. 1

Fig. 2. Synthesis of DHA-HCPT

FIG. 2

Fig. 3. Structurs of camptothecin and related analogues

FIG. 3

ANTICANCER CONJUGATES OF CAMPTOTHECIN AND UNSATURATED FATTY ACIDS

RELATED APPLICATIONS

The present application claims the benefit, under 35 U.S.C. §120, of the U.S. provisional patent application U.S. SNo. 60/401,195, which was filed on Aug. 6, 2002, and U.S. SNo. 60/444,392, which was filed on Feb. 3, 2003, the entire contents of which are hereby incorporated herein by reference.

FIELD OF THE INVENTION

The present invention relates to novel fatty acid derivatives of the camptothecin class of compounds, their methods of preparation and use as antitumor agents.

BACKGROUND OF THE INVENTION

Cancer cells do not contain molecular targets that are completely foreign to the host. Therefore, most anticancer chemotherapies have relied primarily on the enhanced proliferative rate of cancer cells. Anticancer drugs kill the rapidly dividing tumor cells in either S or G2-M phases of the cell cycle while sparing the quiescent tumor and normal cells in G1 or G0 phases (Tannock, I. F. in DeVita et al., eds. Cancer: Principle and Practice of Oncology: 3–13, J. B. Lippincott, Philadelphia, 1989). The fraction of tumor cells that are dividing at any time varies depending upon tumor type and the growth stage of the tumor. In general, faster-cycling tumors e.g., lymphomas, testicular tumors, and some childhood tumors, are more susceptible to chemotherapy than are the more common types of solid tumors with slowly cycling or noncycling cells. However, some normal cells such as bone marrow and intestinal mucosa also cycle rapidly, making them susceptible to the toxic side effects of chemotherapeutic drugs. Thus, finding a unique property of tumor biochemistry or physiology that can be exploited to target chemotherapeutic drugs to tumors to maintain an effective concentration for longer times and thereby create a greater therapeutic advantage is important to a successful cancer therapy. There remains a need in the art for effective cancer therapeutics.

SUMMARY OF THE INVENTION

The present invention provides compounds that can be used for the treatment of mammalian cell proliferating disease, e.g., cancer. The present invention provides conjugates of DHA and camptothecin (CPT) compounds that have a greatly improved therapeutic efficacy, compared to free camptothecin compounds. These DHA-CPT conjugates have been tested in experimental animal tumor models, and shown excellent antitumor activity compared to the free camptothecin compounds. The DHA-CPT compounds provided by this invention can be used to treat cancer. The compounds are of the following formula (I) or pharmaceutically acceptable salts thereof:

Long chain unsaturated fatty acid—linker—CPT    (Formula I)

wherein:
the Long-chain unsaturated fatty acid is $C_{12}$–$C_{22}$ mono or poly unsaturated fatty acids, which include, but are not limited to, palmitoleic acid, oleic acid, linoleic acid, linolenic acid, arachidonic acid, eicosapentaenoic acid (EPA) and docosahexaenoic acid (DHA);

the linker is $-(alkyl)_m-(aryl)_n-C(O)-$ or $-(aryl)_m-(alkyl)_n-C(O)-$; wherein: m and n are independently 0–3, and $m+n \geq 1$; and

CPT is a camptothecin compound with the following general structure (Formula II):

(Formula II)

wherein: $R_1$–$R_5$ are H, halo, OH, $NO_2$, $NH_2$, alkyl, O-alkyl, NH-alkyl, N(alkyl)$_2$, ester, or amide, and can be the same or different. When any of $R_1$–$R_5$ is amino, the compounds are the free bases and their acid addition salts, such as HCl and $H_2SO_4$.

In preferred embodiments of the compounds of formula (I), the fatty acids are DHA and EPA, the linker is selected from formula (III) and CPT is camptothecin, 9-aminocamptothecin, 10-hydroxycamptothecin, 7-ethyl-10-hydroxycamptothecin and 9-N,N-dimethylaminomethyl-10-hydroxycamptothecin, or their acid addition salts, such as HCl and $H_2SO_4$.

Formula III

A preferred composition of the present invention is:

Another preferred composition of the present invention is:

Yet another preferred composition of the present invention is:

The present invention also provides a method for the treatment of mammalian cell proliferating disease, e.g., cancer. The method comprises administering to a patient an effective amount of one of the compounds of the following formula, or pharmaceutically acceptable salts thereof:

Long chain unsaturated fatty acid—linker—CPT (Formula I)

wherein:

the Long-chain unsaturated fatty acid is $C_{12}$–$C_{22}$ mono or poly unsaturated fatty acids, which include, but are not limited to, palmitoleic acid, oleic acid, linoleic acid, linolenic acid, arachidonic acid, eicosapentaenoic acid (EPA) and docosahexaenoic acid (DHA);

the linker is -(alkyl)$_m$-(aryl)$_n$-C(O)— or -(aryl)$_m$-(alkyl)$_n$-C(O)—; wherein: m and n are independently 0–3, and m+n≧1; and CPT is a camptothecin compound with the following general structure (Formula II):

(Formula II)

wherein: $R_1$–$R_5$ are H, halo, OH, $NO_2$, $NH_2$, alkyl, O-alkyl, NH-alkyl, N(alkyl)$_2$, ester, or amide, and can be the same or different. When any of $R_1$–$R_5$ is amino, the compounds are the free bases and their acid addition salts, such as HCl and $H_2SO_4$.

In preferred embodiments of the compounds of formula (I), the fatty acids are DHA and EPA, the linker is selected from formula (III) and CPT is camptothecin, 9-aminocamptothecin, 10-hydroxycamptothecin, 7-ethyl-10-hydroxycamptothecin and 9-N,N-dimethylaminomethyl-10-hydroxycamptothecin, and their acid addition salts, such as HCl and $H_2SO_4$.

Formula III

In a preferred embodiment of the present invention, the method comprises administering to a patient an effective amount of one of the compounds of the following formula, or pharmaceutically acceptable salts thereof:

The compounds of the present invention can also be used as an adjuvant to conventional cancer therapy to treat apoptosis-resistant tumors and in the treatment of other diseases to overcome drug resistance. The compounds of the present invention can be administered simultaneously or sequentially with at least one conventional cancer therapy. The conventional cancer therapy can be radiation therapy, chemotherapy, and/or biologic therapy. Preferred chemotherapy includes an antimetabolite, an alkylating agent, a plant alkaloid, and an antibiotic. Preferred antimetabolite includes methotrexate, 5-fluorouracil, 6-mercaptopurine, cytosine arabinoside, hydroxyurea, and 20-chlorodeoxyadenosine. Preferred alkylating agent includes cyclophosphamide, melphalan, busulfan, cisplatin, carboplatin, chlorambucil, and nitrogen mustards. Preferred plant alkaloid includes vincristine, vinblastine, and VP-16. Preferred antibiotic includes doxorubicin, daunorubicin, mitomycin c, and bleomycin. Alternate preferred chemotherapy includes decarbazine, mAMSA, hexamethylmelamine, mitoxantrone, taxol, etoposide, dexamethasone. Preferred radiation therapy includes photodynamic therapy, radionucleotides, and radioimmunotherapy. Preferred biologic therapy includes immunotherapy, differentiating agents, and agents targeting cancer cell biology.

The above description sets forth rather broadly the more important features of the present invention in order that the detailed description thereof that follows may be understood, and in order that the present contributions to the art may be better appreciated. Other objects and features of the present invention will become apparent from the following detailed description considered in conjunction with the accompanying drawings. It is to be understood, however, that the drawings are designed solely for the purposes of illustration and not as a definition of the limits of the invention, for which reference should be made to the appended claims.

These and other objects of the present invention will be apparent from the detailed description of the invention provided below.

BRIEF DESCRIPTION OF THE DRAWINGS

The present invention will be further understood from the following description with reference to the tables and figures, in which.

DETAILED DESCRIPTION OF THE INVENTION

A. Definitions

As used herein, the term "Aryl" refers to an unsubstituted or substituted aromatic, carbocyclic group. Aryl groups are either single ring or multiple condensed ring compounds. A phenyl group, for example, is a single ring, aryl group. A naphthyl group exemplifies an aryl group with multiple condensed rings. Aryl groups can be substituted with one or more substituents. Nonlimiting examples of such substituents include $NH_2$, $NO_2$, $N(CH_3)_2$, $ONO2$, F, Cl, Br, I, OH, $OCH_3$, $CO_2H$, $CO_2CH_3$, CN, aryl and heteroaryl.

As used herein, the term "Alkyl" refers to unsubstituted or substituted linear, branched or cyclic alkyl carbon chains of up to 15 carbon atoms. Linear alkyl groups include, for example, methyl, ethyl, n-propyl, n-butyl, n-pentyl, n-hexyl, n-heptyl and n-octyl. Branched alkyl groups include, for example, iso-propyl, sec-butyl, iso-butyl, tert-butyl and neo-pentyl. Cyclic alkyl ("cycloalkyl") groups include, for example, cyclopropyl, cyclobutyl, cyclopentyl and cyclohexyl. Alkyl groups can be substituted with one or more substituents. Nonlimiting examples of such substituents include $NH_2$, $NO_2$, $N(CH_3)_2$, $ONO_2$, F, Cl, Br, I, OH, $OCH_3$, $CO_2H$, $CO_2CH_3$, CN, aryl and heteroaryl. The term "Alkyl" also refers to unsubstituted or substituted linear, branched or cyclic chains of up to 15 carbon atoms that contain at least one heteroatom (e.g., nitrogen, oxygen or sulfur) in the chain. Such linear alkyl groups include, for example, $CH_2CH_2OCH_3$, $CH_2CH_2N(CH_3)_2$ and $CH_2CH_2SCH_3$. Branched groups include, for example, $CH_2CH(OCH_3)CH_3$, $CH_2CH(N(CH_3)_2)CH_3$ and $CH_2CH(OCH_3)CH_3$. Such cyclic alkyl groups include, for example, $CH(CH_2CH_2)_2O$, $H(CH_2CH_2)_2NCH_3$ and $CH(CH_2CH_2)_2S$. Such alkyl groups can be substituted with one or more substituents. Nonlimiting examples of such substituents include $NH_2$, $NO_2$, $N(CH_3)_2$, $ONO_2$, F, Cl, Br, I, OH, $OCH_3$, $CO_2H$, $CO_2CH_3$, CN, aryl and heteroaryl.

As used herein, the term "pharmaceutically acceptable" refers to a lack of unacceptable toxicity in a compound, such as a salt or excipient. Pharmaceutically acceptable salts include inorganic anions such as chloride, bromide, iodide, sulfate, sulfite, nitrate, nitrite, phosphate, and the like, and organic anions such as acetate, malonate, pyruvate, propionate, cinnamate, tosylate, citrate, and the like. Pharmaceutically acceptable excipients are described below, and, at length by E. W. Martin, in Remington's Pharmaceutical Sciences Mack Publishing Company (1995), Philadelphia, Pa., 19th ed.

The term "therapeutically effective amount" refers to an amount of the therapeutic compositions of the present invention, e.g., fatty acid camptothecin compounds, capable of inhibiting the proliferation of a mammalian cell, e.g., a cancer cell.

The term "mammalian cell" refers to a cell or cell line derived from a mammalian source. The term "mammalian cell proliferating disease" refers to a condition wherein mammalian cells grow and/or divide in a way or at a rate that differs from that observed in a normal mammalian cell.

B. General Principles of Treatment

The goal of cancer treatment is first to eradicate the cancer. If this primary goal cannot be accomplished, the goal of cancer treatment shifts to palliation, the amelioration of symptoms, and preservation of quality of life while striving to extend life.

Cancer treatments are divided into four main groups: surgery, radiation therapy (including photodynamic therapy), chemotherapy (including hormonal therapy), and biologic therapy (including immunotherapy, differentiating agents, and agents targeting cancer cell biology). The modalities are often used in combination, and agents in one category can act by several mechanisms. For example, cancer chemotherapy agents can induce differentiation, and antibodies (a form of immunotherapy) can be used to deliver radiation therapy. Surgery and radiation therapy are considered local treatments, though their effects can influence the behavior of tumor at remote sites. Chemotherapy and biologic therapy are usually systemic treatments.

Cancer behaves in many ways as an organ that regulates its own growth. However, cancers have not set an appropriate limit on how much growth should be permitted. Normal organs and cancers share the property of having a population of cells in cycle and actively renewing and a population of cells not in cycle. In cancers, cells that are not dividing are heterogeneous; some have sustained too much genetic damage to replicate but have defects in their death pathways that permit their survival; some are starving for nutrients and oxygen; and some are reversibly out of cycle poised to be recruited back into cycle and expand if needed. Severely damaged and starving cells are unlikely to kill the patient. The problem is that the cells that are reversibly not in cycle are capable of replenishing tumor cells physically removed or damaged by radiation and chemotherapy.

Tumors follow a Gompertzian growth curve; the growth fraction of a neoplasm starts at 100% with the first transformed cell and declines exponentially over time until by the time of diagnosis at a tumor burden of 1 to $5 \times 10^9$ tumor cells, the growth fraction is usually 1 to 4%. Cancers try to limit their own growth but are not completely successful at doing so. The peak growth rate occurs before the tumor is detectable. Metastases can be observed to grow more rapidly than the primary tumor, consistent with the idea that an inhibitory factor slows the growth of larger tumor masses. When a tumor recurs after surgery or chemotherapy, frequently its growth is accelerated and the growth fraction of the tumor is increased.

C. Principles of Chemotherapy

Historic Background

Candidate compounds that might have selectivity for cancer cells were suggested by the marrow-toxic effects of sulfur and nitrogen mustards and led, in the 1940s, to the first notable regressions of hematopoietic tumors following use of these compounds. As these compounds caused covalent modification of DNA, the structure of DNA was thereby identified as a potential target for drug design efforts. Biochemical studies demonstrating the requirement of growing tumor cells for precursors of nucleic acids led to studies of folate analogues. The cure of patients with advanced choriocarcinoma by methotrexate in the 1950s provided further impetus to define the value of chemotherapeutic agents in many different tumor types. This resulted in efforts to understand unique metabolic requirements for biosynthesis of nucleic acids and led to the design, rational for the time, of compounds that might selectively interfere with DNA synthesis in proliferating cancer cells. The capacity of hormonal manipulations including oophorectomy and orchiectomy to cause regressions of breast and prostate cancers, respectively, provided a rationale for efforts to interfere with various aspects of hormone function in hormone-dependent tumors. The serendipitous finding that certain poisons derived from bacteria or plants could affect normal DNA or mitotic spindle function allowed completion of the classic armamentatrium of "cancer chemotherapy agents" with proven safety and efficacy in the treatment of certain cancers.

End-Points of Drug Action

Chemotherapy agents may be used for the treatment of active, clinically apparent cancer. Table 1A lists those tumors considered curable by conventionally available chemotherapeutic agents. Most commonly, chemotherapeutic agents are used to address metastatic cancers. If a tumor is localized to a single site, serious consideration of surgery or primary radiation therapy should be given, as these treatment modalities may be curative as local treatments. Chemotherapy may be employed after the failure of these modalities to eradicate a local tumor, or as part of multimodality approaches to offer primary treatment to a clinically localized tumor. In this event, it can allow organ preservation when given with radiation, as in larynx or other upper airway sites; or sensitize tumors to radiation when given, for example, to patients concurrently receiving radiation for lung or cervix cancer (Table 1B). Chemotherapy can be administered as an adjuvant to surgery (Table 1C) or radiation, a use that may have curative potential in breast, colon, or anorectal neoplasms. In this use, chemotherapy attempts to eliminate clinically unapparent tumor that may have already disseminated. Chemotherapy can be used in conventional dose regimens. In general, these doses produce reversible acute side effects primarily consisting of transient myelosuppression with or without gastrointestinal toxicity (nausea), which are readily managed. High-dose chemotherapy regimens are predicated on the observations that the concentration-effect curve for many anticancer agents is rather steep, and increased dose can produce markedly increased therapeutic effect, although at the cost of potentially life-threatening complications that require intensive support, usually in the form of bone marrow or stem cell support from the patient (autologous) or from donors matched for histocompatibility loci (allogeneic). High-dose regimens nonetheless have definite curative potential in defined clinical settings (Table 1D).

The evaluation of a chemotherapeutic agent's benefit can be assessed by carefully quantitating its effect on tumor size and using these measurements to decide objectively the basis for further treatment of a particular patient or further clinical evaluation of a drug's potential. A partial response (PR) is defined conventionally as a decrease by at least 50% in a tumor's bi-dimensional area; a complete response (CR) connotes disappearance of all tumors; progression of disease signifies increase by >25% from baseline or best response; and "stable" disease fits into none of the above categories.

If cure is not possible, chemotherapy may be undertaken with the goal of palliating some aspect of the tumor's effect on the host. Common tumors that have been meaningfully addressed with palliative intent are listed in Table 1E. Usually tumor-related symptoms may manifest as pain, weight loss, or some local symptom related to the tumor's effect on normal structures. Patients treated with palliative intent should be aware of their diagnosis and the limitations of the proposed treatment, have access to suitable palliative strategies in the event that no treatment is elected, and have a suitable "performance status"—according to assessment algorithms such as the one developed by Karnofsky or by the Eastern Cooperative Oncology Group (ECOG). ECOG performance status 0 (PS0) patients are without symptoms; PS1 patients have mild symptoms not requiring treatment; PS2, symptoms requiring some treatment; PS3, disabling symptoms, but allowing ambulation for >50% of the day; PS4, ambulation <50% of the day. Only PS0 to PS2 patients are generally considered suitable for palliative (non-curative) treatment. If there is curative potential, even poor performance status patients may be treated, but their prognosis is usually inferior to those of good performance patients treated with similar regimens.

The usefulness of any drug is governed by the extent to which a given dose causes a useful result (therapeutic effect; in the case of anticancer agents, toxicity to tumor cells) as opposed to a toxic effect. The therapeutic index is the degree of separation between toxic and therapeutic doses. Really useful drugs have large therapeutic indices, and this usually occurs when the drug target is expressed in the disease-causing compartment as opposed to the normal compartment. Classically, selective toxicity of an agent for an organ is governed by the expression of an agent's target; or differential accumulation into or elimination from compartments where toxicity is experienced or ameliorated, respectively. Current antineoplastic agents have the unfortunate property that their targets are present in both normal and tumor tissues. Therefore, antineoplastic agents have relatively narrow therapeutic indices.

In the past, agents with promise for the treatment of cancer have been detected empirically through screening for antiproliferative effects in animal or human tumors in rodent hosts or through inhibition of tumor cells growing in tissue culture. An optimal schedule for demonstrating antitumor activity in animals is defined in further preclinical studies, as is the optimal drug formulation for a given route and schedule. Safety testing in two species on an analogous schedule of administration defines the starting dose for a phase I trial in humans, where escalating doses of the drug are given until reversible toxicity is observed. Dose-limiting toxicity (DLT) defines a dose that conveys greater toxicity than would be acceptable in routine practice, allowing definition of a maximal tolerated dose (MTD). The occurrence of toxicity is correlated if possible with plasma drug concentrations. The MTD or a dose just lower than the MTD is usually the dose suitable for phase II trials, where a fixed dose is administered to a relatively homogeneous set of patients in an effort to define whether the drug causes regression of tumors. An "active" agent conventionally has partial response rates of at least 20 to 25% with reversible non-life-threatening side effects, and it may then be suitable for study in phase III trials to assess efficacy in comparison to standard or no therapy. Response is the immediate indicator of drug effect. To be clinically valuable, responses must translate into effects on overall survival or at least time to progression as important indicators of an ultimately useful drug. More recently, active efforts to quantitate effects of anticancer agents on quality of life as an important outcome are being developed. Cancer drug clinical trials conventionally use a toxicity grading scale where grade I toxicities do not require treatment; grade II often require symptomatic treatment but are not life-threatening; grade III toxicities are potentially life-threatening if untreated; grade IV toxicities are actually life-threatening; and grade V toxicities ultimately lead to patient death.

Cancer arises from genetic lesions that cause an excess of cell growth or division, with inadequate cell death. In addition, failure of cellular differentiation results in altered cellular position and capacity to proliferate while cut off from normal cell regulatory signals. Normally, cells in a differentiated state are stimulated to enter the cell cycle from a quiescent state, or "G0," or continue after completion of a prior cell division cycle in response to environmental cues including growth factor and hormonal signals. Cells progress through G1 and enter S phase after passing through "checkpoints," which are biochemically regulated transition points, to assure that the genome is ready for replication. One important checkpoint is mediated by the p53 tumor-suppressor gene product, acting through its up-regulation of the $p21^{WAF1}$ inhibitor of cyclin-dependent kinase (CDK) function, acting on CDKs 4 or 6. These molecules can also be inhibited by the $p16^{INK4A}$ and $p27^{KIP1}$ CDK inhibitors and, in turn, are activated by cyclins of the D family (which appear during G1) and the proper sequence of regulatory phosphorylations. Activated CDKs 4 or 6 phosphorylate and thus inactivate the product of the retinoblastoma susceptibility gene, pRb, which in its nonphosphorylated state complexes with transcription factors of the E2F family. Phosphorylated pRb releases E2Fs, which activate genes important in completing DNA replication during S phase, progression through which is promoted by CDK2 acting in concert with cylins A and E. During G2, another checkpoint occurs, in which the cell assures the completion of correct DNA synthesis. Cells then progress into M phase under the influence of CDK1 and cyclin B. Cells may then go on to a subsequent division cycle or enter into a quiescent, differentiated state.

Biologic Basis for Cancer Chemotherapy

The classic view of how cancer chemotherapeutic agents cause regressions of tumors focused on models such as the L1210 murine leukemia system, where cancer cells grow exponentially after inoculation into the peritoneal cavity of an isogenic mouse. The interaction of drug with its biochemical target in the cancer cell was proposed to result in "unbalanced growth" that was not sustainable and therefore resulted in cell death, directly because of interacting with the drug's proximal target. Agents could be categorized as cell cycle-active, phase-specific (e.g., antimetabolites, purines, and pyrimidines in S phase; vinca alkaloids in M), and phase-nonspecific agents (e.g., alkylators, and antitumor antibiotics including the anthracyclines, actinomycin, and mitomycin), which can injure DNA at any phase of the cell cycle but appear to then block in G2 before cell division at a checkpoint in the cell cycle. Cells arrested at a checkpoint may repair DNA lesions. Checkpoints have been defined at the G1 to S transition, mediated by the tumor-suppressor gene p53 (giving rise to the characterization of p53 as a "guardian of the genome"); at the G2 to M transition, mediated by the chk1 kinase influencing the function of CDK1; and during M phase, to ensure the integrity of the mitotic spindle. The importance of the concept of checkpoints extends from the hypothesis that repair of chemotherapy-mediated damage can occur while cells are stopped at a checkpoint; therefore, manipulation of checkpoint function emerges as an important basis of affecting resistance to chemotherapeutic agents.

Resistance to drugs was postulated to arise either from cells not being in the appropriate phase of the cell cycle or from decreased uptake, increased efflux, metabolism of the drug, or alteration of the target, e.g., by mutation or overexpression. Indeed, the p170PGP (p170 P-glycoprotein; mdr gene product) was recognized from experiments with cells growing in tissue culture as mediating the efflux of chemotherapeutic agents in resistant cells. Certain neoplasms, particularly hematopoietic tumors, have an adverse prognosis if they express high levels of p170PGP, and modulation of this protein's function has been attempted by a variety of strategies.

Combinations of agents were proposed to afford the opportunity to affect many different targets or portions of the cell cycle at once, particularly if the toxic effects for the host of the different components of the combination were distinct. Combinations of agents were actually more effective in animal model systems than single agents, particularly if the tumor cell inoculum was high. This thinking led to the design of "combination chemotherapy" regimens, where drugs acting by different mechanisms (e.g., an alkylating agent plus an antimetabolite plus a mitotic spindle blocker) were combined. Particular combinations were chosen to emphasize drugs whose individual toxicities to the host were, if possible, distinct.

This view of cancer drug action is grossly oversimplified. Most tumors do not grow in an exponential pattern but rather follow Gompertzian kinetics, where the rate of tumor growth decreases as tumor mass increases. Thus, a tumor has quiescent, differentiated compartments; proliferating compartments; and both well-vascularized and necrotic regions. In addition, cell death is itself now understood to be a closely regulated process. Necrosis refers to cell death induced, for example, by physical damage with the hallmarks of cell swelling and membrane disruption. Apoptosis, or programmed cell death, refers to a highly ordered process whereby cells respond to defined stimuli by dying, and it recapitulates the necessary cell death observed during the ontogeny of the organism. Anoikis refers to death of epithelial cells after removal from the normal milieu of substrate, particularly from cell-to-cell contact. Cancer chemotherapeutic agents can cause both necrosis and apoptosis. Apoptosis is characterized by chromatin condensation (giving rise to "apoptotic bodies"); cell shrinkage; and, in living animals, phagocytosis by surrounding stromal cells without evidence of inflammation. This process is regulated either by signal transduction systems that promote a cell's demise after a certain level of insult is achieved or in response to specific cell-surface receptors that mediate cell death signals. Modulation of apoptosis by manipulation of signal transduction pathways has emerged as a basis for understanding the actions of currently used drugs and designing new strategies to improve their use.

The current view envisions that the interaction of a chemotherapeutic drug with its target causes or is itself a signal that initiates a "cascade" of signaling steps to trigger an "execution phase" where proteases, nucleases, and endogenous regulators of the cell death pathway are activated. Effective cancer chemotherapeutic agents are efficient activators of apoptosis through signal transduction pathways. While apoptotic mechanisms are important in regulating cellular proliferation and the behavior of tumor cells in vitro, in vivo it is unclear whether all of the actions of chemotherapeutic agents to cause cell death can be attributed to apoptotic mechanisms. However, as reviewed below, changes in molecules that regulate apoptosis are clearly correlated with clinical outcomes (e.g., overexpression of Bcl-2 and related proteins).

Chemotherapeutic Agents Used for Cancer Treatment

Table 2 lists commonly used cancer chemotherapy agents and pertinent clinical aspects of their use. The drugs may be usefully grouped into three general categories: those affecting DNA, those affecting microtubules, and those acting at hormone-like receptors.

DHA-paclitaxel Conjugate

Sauer et al (Cancer Res., 42: 4090, 1982; Sauer and Dauchy, Biochem. Soc. Trans., 18: 80, 1990, each incorporated herein by reference) studied the uptake of fatty acids and other metabolic precursors by tumor cells in tissue-isolated hepatomas with a single arterial inflow and a single venous outflow. In these systems, tumors avidly took up certain kinds of natural fatty acids from the arterial blood, presumably for use as biochemical precursors and energy sources (Sauer et al., Cancer Res., 42: 4090, 1982; Sauer and Dauchy, Biochem. Soc. Trans., 18: 80, 1990; Brit. J. Cancer, 66: 297, 1992, each incorporated herein by reference). Based on these observations, a conjugate of cis4,7,10,13,16,19-docosahexenoic acid (DHA) and paclitaxel, DHA-paclitaxel, was synthesized to target paclitaxel to tumors to decrease toxicity to normal tissues and increase the therapeutic index relative to free paclitaxel (Bradley et al., Clin. Cancer Res., 7: 3229, 2001, incorporated herein by reference). DHA-paclitaxel was reported to have enhanced therapeutic efficacy compared to free paclitaxel in both the experimental animal tumor models and in human clinical trials (Bradley et al., Clin. Cancer Res., 7: 3229, 2001).

Although the therapeutic index of DHA-paclitaxel is superior to free paclitaxel; the water-solubility of the former was greatly reduced due to the addition of the highly hydrophobic DHA moiety, resulting in difficulty in formulation. Free paclitaxel hardly dissolves in water. As a result, it is currently formulated with Cremophor, which causes a number of toxic effects in patients.

In the present invention, it was hypothesized that, by adding a functional group that increases the agent's water-solubility when conjugated to the DHA moiety to produce a conjugate with increased water-solubility, the resulting chemotherapeutic conjugates would have significantly improved therapeutic efficacy compared to the free chemotherapeutic agents.

DHA-CPT Conjugates

Camptothecin (CPT) is a natural alkaloid, which was first isolated in 1966 from the extract of a Chinese plant, *Camptotheca accuminata*, by Wall et al (J. Am. Chem. Soc., 88: 3888, 1966, incorporated herein by reference). The CPT class of compounds is among the most promising new drugs for treatment of human cancers (Potmesil M, Pinedo H, eds. *Camptothecins: New Anticancer Agents*. CRC Press, Boca Raton, 1995, incorporated herein by reference).

DNA topoisomerase I is a nuclear enzyme, which covalently binds to double-stranded DNA, forming a cleavable complex and producing a single-strand break (Champoux J. J., J. Mol. Biol., 118: 441, 1978). This cleavable complex facilitates the relaxation of torsional strain of the supercoiled DNA. Once the torsional strain has been relieved, the enzyme rejoins the cleaved strand of DNA and dissociates from the relaxed double helix (Stivers et al., Biochemistry, 36: 5212, 1997). The CPT compounds bind to and stabilize the cleavable complex (Hsiang et al., J. Biol. Chem., 260: 14873, 1985; Hsiang Y. H. and Liu L. F., Cancer Res., 48: 1722, 1988), and inhibit the religation of the DNA strain, leading to an accumulation of DNA single-stranded breaks. The single-stranded breaks are not in themselves toxic to the cell, because the strands readily religate on drug removal; however, collision of the DNA replication fork with the drug-enzyme-DNA complex generates an irreversible double-strand break that ultimately leads to cell death (Tsao et al., Cancer Res., 53: 5908, 1993). Thus, the CPT compounds are S phase-specific, because ongoing DNA synthesis is needed to induce the above sequence of events leading to cytotoxicity. This mechanism of action has significant implications for the use of these agents. It suggests that a prolonged exposure of the camptothecin compounds to tumors is needed to ensure their optimal therapeutic efficacy.

Both a prolonged exposure of the CPT compounds to the tumor and a tumor-targeted delivery of these compounds will increase their therapeutic efficacy. Because cancer cells do not contain molecular targets that are completely foreign to the host, tumor-targeted delivery of anticancer agents has not made significant clinical success.

In the initial clinical trials of CPT, activity was limited by its poor solubility in physiologically compatible media. Early attempts to form a water-soluble sodium salt of CPT by opening the lactone ring with sodium hydroxide resulted in a compound having poor antitumor activity (Gottlieb, et al., Cancer Chemother. Rep., 54: 461, 1970; Moertel, et al., Cancer Chemother. Rep., Part 1, 56: 95, 1972; Muggia, et al., Cancer Chemother. Rep., 56: 515, 1972, each incorporated herein by reference). It was later reported that the closed lactone-form is an absolute requirement for antitumor activity (Wani, et al., J. Med. Chem., 23: 554, 1980, incorporated herein by reference). Intensive efforts in medicinal chemistry over the past several decades have provided a large number of camptothecin derivatives, of which topotecan and irinotecan are now approved for the treatment of cancer in the United States. Irinotecan is the first FDA-approved novel colorectal cancer treatment in over 40 years, and is indicated as a component of the first-line combination therapy for patients with metastatic colorectal cancer. Irinotecan is also used for treatment of other cancers such as cervical cancer, esophageal cancer, gastric cancer, glioma, lung cancer, pancreatic cancer and mesothelioma.

Although the marketed CPT drugs show excellent antitumor activities and are very useful as a cancer treatment, they are strictly restricted in clinical use because of their severe side effects. Thus, new CPT derivatives that have good antitumor activities with different bio-distribution and pharmacokinetic profiles are needed for the treatment of various types of cancers.

Synthesis of simple saturated long-chain fatty acid esters of 10-hydroxycamptothecin has been reported (Takayama et al., Bioorg. Med. Chem. Lett., 8: 415, 1998, incorporated herein by reference). These compounds are hydrolyzed by carboxylate esterase in vitro. These simple esters of 10-hydroxycamptothecin are difficult to formulate due to the addition of a hydrophobic fatty acid moiety, and the compounds are not expected to have a significantly increased therapeutic efficacy because they are not selectively taken up by tumors or have a much-prolonged half-life. The in vivo antitumor activity of these compounds is not disclosed.

The CPT class of compounds is among the most promising cytotoxic drugs, which acts by inhibiting topoisomerase I, an enzyme important for DNA synthesis and repair. The marketed CPT drugs have antitumor activity; however, they also cause severe side effects. Because tumor cells selectively accumulate DHA, it was hypothesized in the present invention that conjugating DHA to CPT would further increases therapeutic efficacy and reduce toxicity due to selective tumor targeting.

The present invention provides compounds of the formula:

Long chain unsaturated fatty acid—linker—CPT    (Formula I)

wherein:
the Long-chain unsaturated fatty acid is $C_{12}$–$C_{22}$ mono or poly unsaturated fatty acids, which include, but are not limited to, palmitoleic acid, oleic acid, linoleic acid, linolenic acid, arachidonic acid, eicosapentaenoic acid (EPA) and docosahexaenoic acid (DHA);
the linker is -(alkyl)$_m$-(aryl)$_n$-C(O)- or -(aryl)$_m$-(alkyl)$_n$-C(O)—; wherein: m and n are independently 0–3, and m+n≧1; and
CPT is a camptothecin compound with the following structure (Formula II):

wherein: $R_1$–$R_5$ are H, halo, OH, $NO_2$, $NH_2$, alkyl, O-alkyl, NH-alkyl, N(alkyl)$_2$, ester, or amide, and can be the same or different. When any of $R_1$–$R_5$ is amino, the compounds are the free bases and their acid addition salts, such as HCl and $H_2SO_4$.

In preferred embodiments of the compounds of formula (I), the fatty acids are DHA and EPA, the linker is selected from formula (III), and CPT, as it is referred to in the present invention, includes the plant alkaloid 20(S)-camptothecin, water insoluble or substantially water insoluble analogs, derivatives, prodrugs and pharmaceutically active metabolites of 20(S)-camptothecin. Examples of camptothecin derivatives include, but are not limited to, 9-nitrocamptothecin, 9-aminocamptothecin, 9-methylcamptothecin, 9-chlorocamptothecin, 9-fluorocamptothecin, 7-ethylcamptothecin, 10-methylcamptothecin, 10-chlorocamptothecin, 10-bromocamptothecin, 10-fluorocamptothecin, 9-methoxycamptothecin, 11-fluorocamptothecin, 10-hydroxycamptothecin, 7-ethyl-10-hydroxycamptothecin, 9-N,N-dimethylaminomethyl-10-hydroxycamptothecin, 10,11-methylenedioxycamptothecin, and 10,11-ethylenedioxycampto-thecin, and 7-(4-methylpiperazinomethylene)-10,11-methylenedioxycamptothecin. Prodrugs of camptothecin include, but are not limited to, esterified camptothecin derivatives, such as camptothecin 20-O-propionate, camptothecin 20-O-butyrate, camptothecin 20-O-glycinate, camptothecin 20-O-valerate, camptothecin 20-O-heptanoate, camptothecin 20-O-nonanoate, camptothecin 20-O-crotonate, camptothecin 20-O-2',3'-epoxybutyrate, nitrocamptothecin 20-O-acetate, nitrocamptothecin 20-O-propionate, and nitrocamptothecin 20-O-butyrate.

Formula III

The compounds of the present invention are effective for the treatment of mammalian cell proliferating disease, e.g., cancer. The compounds of the present invention have increased half-life in vivo, and are accumulated by proliferating mammalian cells, e.g., tumor cells. As a result of their increased half-life in vivo and proliferating cell-selective accumulation, e.g., tumor-selective accumulation, these compounds are more effective in treating cancer, and have decreased side effects. The present invention provides new CPT agents, which show a very high antitumor efficacy with low toxicity.

DHA-CC-1065 Conjugates

The CC-1065 compounds including the naturally occurring CC-1065 and their synthetic analogues adozelesin, bizelesin, carzelesin (Aristoff, P. A. Adv. Med. Chem., 2: 67, 1993) belong to one of the most potent class of antitumor agents ever discovered. These compounds are 100–10,000-fold more potent than doxorubicin.

In the present invention, conjugates of DHA and CC-1065 analogues were synthesized and their antitumor effects were evaluated in vitro and in experimental animal tumor models. Despite the high potency of the CC-1065 compounds, the DHA-CC-1065 conjugates did not show significant improvement in therapeutic efficacy compared to the free drug. These experimental data demonstrate that not all conjugates of DHA and anticancer agents will have a highly enhanced therapeutic efficacy compared to the free drug, suggesting that the excellent antitumor efficacy of the conjugates of DHA and camptothecin provided by this invention cannot have been foreseen based on the works of Bradley et al. (Bradley et al., Clin. Cancer Res., 7: 3229, 2001).

D. Formulations and Methods of Treatment

Compositions intended for oral use may be prepared according to any method known to the art for the manufacture of pharmaceutical compositions and such compositions may contain one or more compounds selected from the group consisting of sweetening compounds, flavoring compounds, coloring compounds and preserving compounds in order to provide pharmaceutically elegant and palatable preparations. Tablets contain the active compound in a mixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating compounds, for example, corn starch, or alginic acid; binding compounds, for example starch, gelatin or acacia, and lubricating compounds, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active material in admixture with excipients suitable for the manufacture of aqueous suspensions. Such excipients are suspending compounds, for example sodium carboxymethylcellulose, methylcellulose, hydropropylmethylcellulose, sodium alginate, polyvinylpyrrolidone, gum tragacanth and gum acacia; dispersing or wetting compounds may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring compounds, one or more flavoring compounds, and one or more sweetening compounds, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening compound, for example beeswax, hard paraffin or acetyl alcohol. Sweetening compounds such as those set forth above, and flavoring compounds may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting compound, suspending compound and one or more preservatives. Suitable dispersing or wetting compounds and suspending compounds are exemplified by those already mentioned above. Additional excipients, for example sweetening, flavoring and coloring compounds, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying compounds may be naturally occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example sweetening, flavoring and coloring compounds, may also be present.

Syrups and elixirs may be formulated with sweetening compounds, for example glycerol, propylene glycol, sorbitol or sucrose. Such formulations may also contain a demulcent, a preservative and flavoring and coloring compounds. The pharmaceutical compositions may be in the form of a sterile injectable aqueous or oleaginous suspension. This suspension may be formulated according to the known art using those suitable dispersing or wetting compounds and suspending compounds which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The active compound may also be administered in the form of suppositories for rectal administration of the drug. These compositions can be prepared by mixing the drug with a suitable non-irritating excipient,. which is solid at ordinary temperatures but liquid at the rectal temperature and will therefore melt in the rectum to release the drug. Such materials are cocoa butter and polyethylene glycols.

The active compound may be administered parenterally in a sterile medium. The drug, depending on the vehicle and concentration used can either be suspended or dissolved in the vehicle. Advantageously, adjuvants such as local anesthetics, preservatives and buffering compounds can be dissolved in the vehicle.

Compositions of the present invention (i.e., fatty acid CPT derivatives as defined above in Formulas I, II, and III) may be administered continuously or intermittently by any route which is compatible with the particular molecules. Thus, as appropriate, administration may be oral or parenteral, including subcutaneous, intravenous, inhalation, nasal, and intraperitoneal routes of administration. In addition, intermittent administration may be by periodic injections of a bolus of the composition once daily, once every two days, once every three days, once weekly, twice weekly, biweekly, twice monthly, and monthly.

Therapeutic compositions of the present invention may be provided to an individual by any suitable means, directly (e.g., locally, as by injection, implantation or topical administration to a tissue locus) or systemically (e.g., parenterally or orally). Where the composition is to be provided parenterally, such as by intravenous, subcutaneous, intramolecular, ophthalmic, intraperitoneal, intramuscular, buccal, rectal, vaginal, intraorbital, intradermal, transdermal, intratracheal, intracerebral, intracranial, intraspinal, intraventricular, intrathecal, intracisternal, intracapsular, intranasal or by aerosol administration, the composition preferably comprises part of an aqueous or physiologically compatible fluid suspension or solution. Thus, the carrier or vehicle is physiologically acceptable so that in addition to delivery of the desired composition to the patient, it does not otherwise adversely affect the patient's electrolyte and/or volume balance. The fluid medium for the agent thus can comprise normal physiologic saline (e.g., 0.9% aqueous NaCl) or a buffer, pH 3–7.4. Alternatively, the use of continuous or pulsatile administration of the therapeutic compositions of the present invention by mini-pump can be employed in the methods of the present invention.

Useful solutions for parenteral administration may be prepared by any of the methods well known in the pharmaceutical art, described, for example, in Remington's Pharmaceutical Science (Gennaro, A., ed.), Mack Pub., 1990. Formulations of the therapeutic agents of the invention may include, for example, polyalkylene glycols such as polyethylene glycol, oils of vegetable origin, hydrogenated naphthalenes, and the like. Formulations for direct administration, in particular, may include glycerol and other compositions of high viscosity to help maintain the agent at the desired locus. Biocompatible, preferably bioresorbable, polymers, including, for example, hyaluronic acid, collagen, tricalcium phosphate, polybutyrate, lactide, and glycolide polymers and lactide/glycolide copolymers, may be useful excipients to control the release of the agent in vivo. Other potentially useful parenteral delivery systems for these agents include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, methoxysalicylate for rectal administration, or cutric acid for vaginal administration. Suppositories for rectal administration may also be prepared by mixing the therapeutic compositions of the present invention (alone or in combination with a chemotherapeutic agent) with a non-irritating excipient such as cocoa butter or other compositions that are solid at room temperature and liquid at body temperatures.

Where the fatty acid camptothecin compound is given by injection, it can be formulated by dissolving, suspending or emulsifying it in an aqueous or nonaqueous solvent. Methyl sulfoxide, N,N-dimethylacetamide, N,N-dimethylformamide, vegetable or similar oils, synthetic aliphatic acid glycerides, esters of higher aliphatic acids and proylene glycol are examples of nonaqueous solvents. The compound is preferably formulated in aqueous solutions such as Hank's solution, Ringer's solution or physiological saline buffer.

Where the fatty acid camptothecin compound is given orally, it can be formulated through combination with pharmaceutically acceptable carriers that are well known in the art. The carriers enable the compound to be formulated, for example, as a tablet, pill, suspension, liquid or gel for oral ingestion by the patient. Oral use formulations can be obtained in a variety of ways, including mixing the compound with a solid excipient, optionally grinding the resulting mixture, adding suitable auxiliaries and processing the granule mixture. The following list includes examples of excipients that can be used in an oral formulation: sugars such as lactose, sucrose, mannitol or sorbitol; cellulose preparations such as maize starch, wheat starch, potato starch, gelatin, gum tragacanth, methyl cellulose, hydroxyproylmethyl-cellulose, sodium carboxymethylcellulose and polyvinylpyrrolidone (PVP).

The fatty acid camptothecin compounds of the present invention can also be delivered in an aerosol spray preparation from a pressurized pack, a nebulizer or from a dry powder inhaler. Suitable propellants that can be used in a nebulizer include, for example, dichlorodifluoro-methane, trichlorofluoromethane, dichlorotetrafluoroethane and carbon dioxide. The dosage can be determined by providing a valve to deliver a regulated amount of the compound in the case of a pressurized aerosol.

Formulations for topical administration to the skin surface may be prepared by dispersing the molecule capable of releasing the therapeutic compositions of the present invention (alone or in combination with a chemotherapeutic agent) with a dermatologically acceptable carrier such as a lotion, cream, ointment or soap. Particularly useful are carriers capable of forming a film or layer over the skin to localize application and inhibit removal. For topical, administration to internal tissue surfaces, the agent may be dispersed in a liquid tissue adhesive or other substance known to enhance adsorption to a tissue surface. For example, hydroxypropylcellulose or fibrinogen/thrombin solutions may be used to advantage. Alternatively, tissue-coating solutions, such as pectin-containing formulations may be used.

The compounds of the present invention can be used in the treatment of cancer and other mammalian cell proliferating diseases. The compounds of the present invention can be provided simultaneously or sequentially in time. The compounds of the present invention can be administered alone or in combination with other therapeutic agents, e.g., chemotherapeutic compounds.

Pharmaceutical compositions of the present invention contain a therapeutically effective amount of the fatty acid camptothecin compounds. The amount of the compound will depend on the patient being treated. The patient's weight, severity of illness, manner of administration and judgment of the prescribing physician should be taken into account in deciding the proper amount. The determination of a therapeutically effective amount of a fatty acid camptothecin compound is well within the capabilities of one with skill in the art.

Although a therapeutically effective amount of a fatty acid camptothecin compound will vary according to the patient being treated, suitable doses will typically be in the range between about 1 mg/kg and 1 g/kg of the compound.

In some cases, it may be necessary to use dosages outside of the stated ranges to treat a patient. Those cases will be apparent to the prescribing physician. Where it is necessary, a physician will also know how and when to interrupt, adjust or terminate treatment in conjunction with a response of a particular patient.

The invention is further defined by reference to the following examples, which are not meant to limit the scope of the present invention. It will be apparent to those skilled in the art that many modifications, both to the materials and to methods, may be practiced without departing from the purpose and interest of the invention. Compounds of the present invention may be tested for efficacy in vitro and in experimental animal tumor models using the assay described below; an effective compound will inhibit tumor growth both in vitro and in experimental animal tumor models. Compounds most preferred in the invention are those that have the greatest antitumor effects in experimental animal tumor models.

EXAMPLES

Example 1

Figure 1:
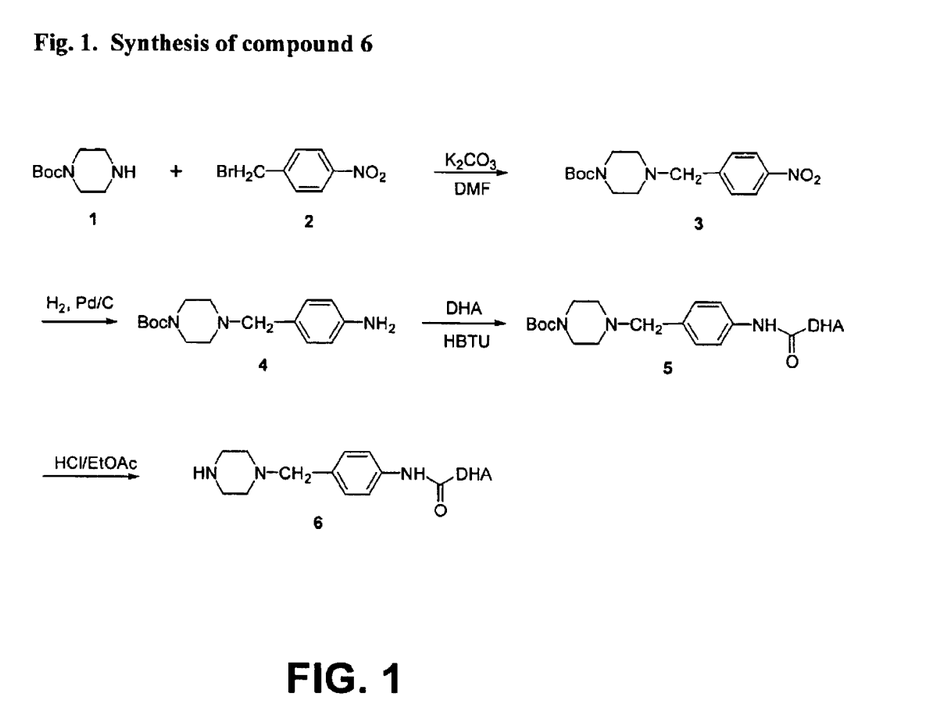
FIG. 1 shows the synthesis of compound 6.

Synthesis of compound 3 tert-Butyl 4-(4-nitrobenzyl)-1-piperazinecarboxylate (3).

To a solution of tert-butyl 1-piperazinecarboxylate, 1 (0.74 g, 4 mmol), and 4-nitrobenzyl bromide, 2 (0.86 g, 4 mmol), in N,N-dimethylformamide (DMF, 5 mL) was added potassium carbonate (3 g), and the reaction mixture was stirred at room temperature for 4 h. The product was extracted with ethyl acetate (50 mL), and the organic phase was washed with water (20 mL×3). The solution was dried with sodium sulfate, and solvent was removed in vacuo. The product was purified by column chromatography, eluting with ethyl acetate to afford 3 as a solid (1.22 g, 95% yield), mp 99–100° C. $^1$H NMR (DMSO-d6): 8.21–8.19 (d, 2H, J=8.8 Hz, Ar-H), 7.61–7.59 (d, 2H, J=8.0 Hz, Ar-H), 3.63 (s, 2H, CH$_2$), 3.34–3.30 (m, 4H, partially obscured, 2×CH$_2$), 2.35–2.3 (m, 4H, 2×CH$_2$), 1.39 (s, 9H, 3×CH$_3$). Anal. (C$_{16}$H$_{23}$N$_3$O$_4$) C, H, N.

Example 2

Synthesis of Compound 5 tert-Butyl 4-[4-(cis4,7,10,13,16,19-docosahexenoyl) amino]benzyl-1-piperazinecarb-oxylate (5).

To compound 3 (0.68 g, 2.1 mmol) in ethyl acetate (100 mL) was added 10% Pd/C (0.1 g), and the reaction mixture was hydrogenated for 2 h under a pressure of 60 lb/inch$^2$. The product was filtered, and solvent was removed in vacuo to afford amine 4 (0.6 g, 97% yield). Without further purification, to amine 4 (0.6 g, 2.06 mmol) dissolved in acetonitrile (90 mL) was added cis-4,7,10,13,16,19-docosahexenoic acid (DHA, 0.67 g, 2.0 mmol), 2-(1-benzotriazol-1-yl)-1,1,3,3-tetramethyluronium hexafluorophosphate (HBTU, 0.94 g, 2.5 mmol), and N,N-diisopropylethylamine (2.1 mL). The reaction mixture was stirred overnight. Solvent was removed in vacuo, and the product was purified by column chromatography, eluting with ethyl acetate to afford 5 as an oil (0.91 g, 73% yield).

$^1$H NMR (DMSO-d6): 9.84 (s, 1H, NH), 7.53–7.51 (d, 2H, J=8.80 Hz, Ar-H), 7.19–7.17 (d, 2H, J=8.40 Hz, Ar-H), 5.35–5.31 (m, 12H, CH═CH), 3.40 (s, 2H, CH$_2$), 3.29 (brs, 4H, 2×CH$_2$), 2.83–2.75 (m, 10H, 5×CH$_2$), 2.35 (brs, 4H, 2×CH$_2$), 2.27 (t, 4H, J=4.80 Hz, 2×CH$_2$), 2.04–2.00 (m, 2H, CH$_2$), 1.38 (s,9H, 3×CH$_3$), 0.91 (t, 3H, J=7.20 Hz, CH$_3$). Anal. (C$_{38}$H$_{55}$N$_3$O$_3$.4.1.H$_2$O) C, H, N

Example 3

Synthesis of Compound 6

1-[4-(cis4,7,10,13,16,19-Docosahexenoyl)amino] benzylpiperazine (6).

Compound 5 (0.85 g, 1.4 mmol) was dissolved in ethyl acetate (10 mL), and saturated anhydrous HCl in ethyl acetate (7 mL) was added. The reaction mixture was stirred at room temperature for 30 min. The precipitate was filtered and washed with ethyl ether to afford 6 (0.68 g, 90% yield). The product was used for the next reaction without further purification.

Example 4

Synthesis of Compound 8

Figure 2:
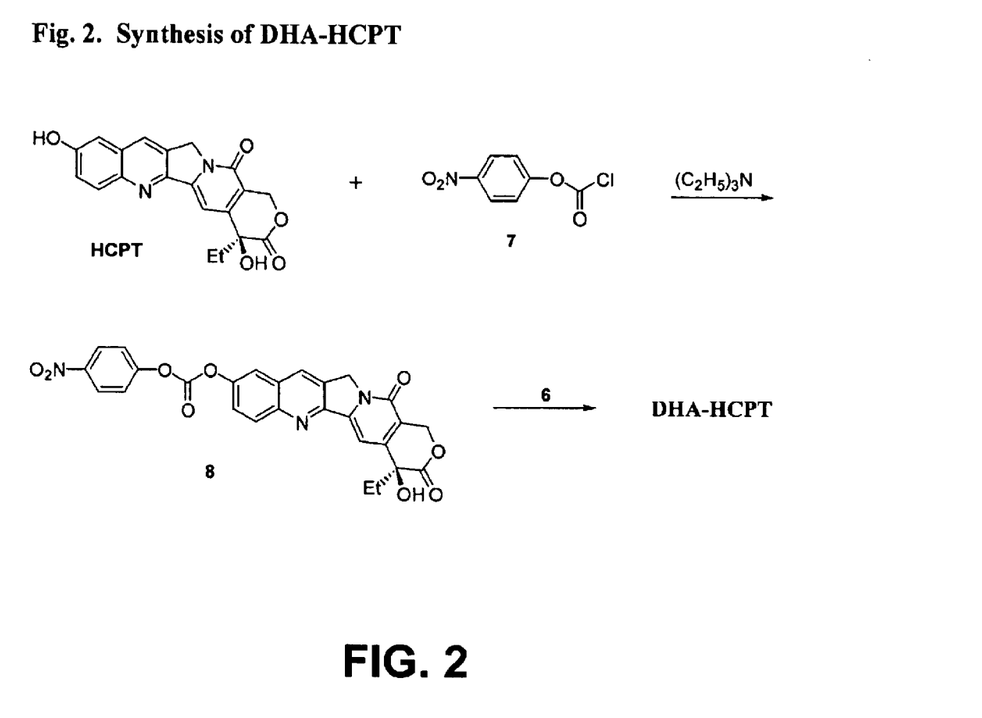
FIG. 2 shows the synthesis of DHA-HCPT.
Figure 3:
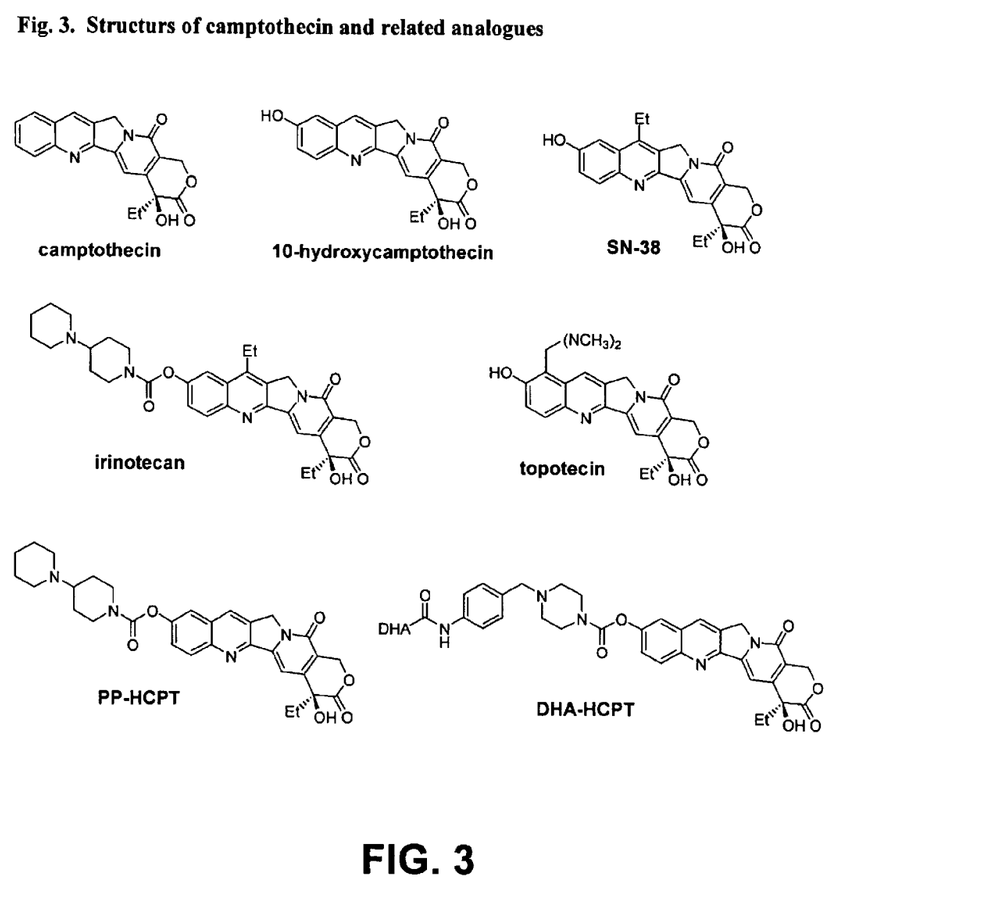
FIG. 3 shows the structures of camptothecin, 10-hydrocamptothecin, SN-38, irinotecan, topotecan, DHA-HCPT and PP-HCPT.

10-(-4-Nitrophenyloxy)carbonyloxycamptothecin (8).

HCPT (25 mg, 0.069 mmol) in tetrahydrofuran (THF, 5 mL) was treated with 4-nitrophenyl chloroformate (54 mg, 0.27 mmol), 7, and triethylamine (0.1 mL), and the reaction was allowed to proceed at room temperature for 1 h. The product was extracted with ethyl acetate (20 mL), and the organic phase was washed with water (10 mL×3). The solution was dried with sodium sulfate, and solvent was removed in vacuo. The product was purified by column chromatography, eluting with ethyl acetate to afford 8 as a yellow solid (33 mg, 91% yield). The product was used for the next reaction without further purification.

Example 5

Synthesis of DHA-HCPT

10-[4-[[4-(cis-4,7,10,13,16,19-Docosahexenoyl)amino] benzyl]-1-piperazino]carbonyl-oxycamptothecin (DHA-HCPT).

Carbonate 8 (0.66 g, 1.25 mmol) in THF (60 mL) was treated with amine 6 (0.85 g, 1.58 mmol) in the presence of triethylamine (2.4 mL), and the reaction mixture was stirred at room temperature for 2 h. Solvent was removed in vacuo, and the product was purified by column chromatography, eluting with ethyl acetate and methanol (15:1, v/v) to afford DHA-HCPT as a yellow solid (0.8 g, 72% yield), mp 196–199° C. $^1$H NMR (DMSO-d6): 9.89 (s, 1H, Ar-H), 8.66–7.26 (m, 8H, Ar-H), 6.55 (s, 2H), 5.43–5.30 (m, 12H), 3.49–3,34 (m, 16H), 2.83 (s, 4H), 2.52–2.34 (m, 8H), 1.88 (t, 1H, J=7.20 Hz), 9.91–0.87 (m, 6H). MS m/z (M$^+$+H): 893.0. The product was dissolved in a mixture of THF and ethyl acetate, and anhydrous HCl in ethyl acetate was then added. The precipitate was filtered, and dried to afford DHA-HCPT as an HCl salt, mp 230° C. (dec.). Anal. (C$_{54}$H$_{61}$N$_5$O$_7$.HCl.5H$_2$O) C, H, N.

Example 6

Synthesis of PP-HCPT

10-[4-(1-Piperidino)-1-piperidino] carbonyloxycamptothecin (PP-HCPT).

Carbonate 8 (0.53 g, 1 mmol) in THF (55 mL) was treated with 4-piperidinopiperidine (0.17 g, 1 mmol), and triethylamine (1 mL), and the reaction was stirred at room temperature for 2 h. Solvent was removed in vacuo, and the product was purified by column chromatography, eluting with dichloromethane and methanol (5:1, v/v) to afford PP-HCPT as a yellow solid (0.41 g, 73% yield). $^1$H NMR (DMSO-d6): 8.66 (s, 1H), 8.19–8.17 (d, 1H, J=9.2 Hz), 7.92–7.91 (d, 1H,J=2.8 Hz), 7.70–7.67 (dd, 1H, J=3.2, 9.6 Hz), 7.35 (s, 1H), 6.54 (s, 1H), 5.44 (s, 2H), 5.30 (s, 2H), 4.29–4.26 (br d, 1H), 4.12–4.08 (br d, 1H), 3.08–3.05 (br t, 1H), 2.94–2.91 (br t, 1H), 1.91–1.82 (m, 4H), 1.53–1.42 (br d, 8H), 0.91–0.87 (t, 3H, J=7.4 Hz). MS m/z (M$^+$+H): 559.64. The product was dissolved in a mixture of THF and ethyl acetate, and anhydrous HCl in ethyl acetate was then added. The precipitate was filtered, and dried to afford PP-HCPT as an HCl salt, mp 235° C. (dec.). Anal. ($C_{31}H_{34}N_4O_6 \cdot HCl \cdot 3H_2O$) C, H, N.

Example 7
Anticancer Activity Assay In Vitro

The antitumor activity of DHA-HCPT was evaluated in vitro against L1210 leukemia cells (Table 3). L1210 leukemia cells ($2.5 \times 10^4$ cells/well) in RPMI-1640 medium supplemented with 10% FCS medium were seeded in a 96-well plate. Drugs (10 μL) at increasing concentrations were added to each well, and the total volume was adjusted to 0.1 mL/well using the same medium. HCPT was used as a positive control. The plate was incubated for 24 h at 37° C. followed by addition of 10 μL of $^3$H-thymidine (20 μCi/mL). The plate was incubated for another 24 h. The cells were harvested, and radioactivity was counted using the Packard Matrix 96 beta counter. The results were expressed as the minimal concentration that inhibits $^3$H-thymidine incorporation by 50% ($IC_{50}$). Percent growth inhibition was calculated as follows: [(total cpm—experimental cpm)/total cpm]×100. In this 48-h cell growth inhibition assay, DHA-HCPT had an $IC_{50}$ value of 1.8 μM, which was 8-fold less potent than its parent HCPT with an $IC_{50}$ value of 0.23 μM. PP-HCPT was 16- and 128-fold less potent than DHA-HCPT and HCPT, respectively with an $IC_{50}$ value of 30 μM. Doxorubicin (Dox) was used as a positive control. Both HCPT and DHA-HCPT caused DNA fragmentation and cells died by apoptosis (data not shown).

Example 8
Anticancer Activity in the L1210 Leukemia Tumor Model

The compounds were tested in male $BDF_1$ mice (18–22 g, 6 mice/group) bearing L1210 leukemia cells. Tumor lines were propagated in DBA/2 female mice with cell ($10^5$ cells/mouse) transfer every 7 days. Diluted ascitic fluid (0.1 mL) containing $10^5$ leukemia cells were inoculated, i.p. in mice on day 0. Mice were injected with 0.1 mL of drug preparation. In this L1210 leukemia model, when one dose was administered, DHA-HCPT was much more efficacious than its parent HCPT (Table 4). For example, at the optimal dose (best therapeutic efficacy and bodyweight loss ≦15% and/or toxic death ≦15%), HCPT had a 77% increase in life span (ILS) with no long-term survivors. In contrast, DHA-HCPT had an ILS of 154% with two long-term survivors at a dose of 180 mg/kg. At an equimolar dose, DHA-HCPT (40 mg/kg) had a much higher therapeutic efficacy (ILS: 108%) than HCPT (15 mg/kg, ILS: 77%). Furthermore, DHA-HCPT had a greatly decreased toxicity compared to HCPT (bodyweight loss of 10% for HCPT vs. a 2% gain for DHA-HCPT).

To find out if the enhanced therapeutic index of DHA-HCPT is simply due to the addition of a carbamate moiety to HCPT, as in the case of irinotecan and its free drug SN-38. A conjugate of HCPT and piperidinopiperidine, PP-HCPT, was synthesized, and its antitumor activity was evaluated against L1210 leukemia in mice. The results in Table 4 clearly show that PP-HCPT is better than HCPT. For example, although PP-HCPT at 73 mg/kg and HCPT at 15 mg/kg have the same ILS (77%), PP-HCPT is much less toxic (weight gain of 2%) to the animal than HCPT (weight loss of 10%). At an equimolar dose, the therapeutic efficacy of DHA-HCPT (60 mg/kg, ILS: 138%) is three-times higher than that of PP-HCPT (37 mg/kg, ILS: 46%). At an equitoxic dose, DHA-HCPT (40 mg/kg) had an ILS of 108% while the ILS produced by PP-HCPT (73 mg/kg) was only 77%. Furthermore, on a molar basis, 40 mg of DHA-HCPT is only ⅓ of 73 mg of PP-HCPT. These results demonstrate that DHA-HCPT is better than PP-HCPT, suggesting that conjugating DHA to HCPT leads to an increased therapeutic index.

DHA-HCPT was also tested using multiple doses (days 1, 5 and 9). At a dose of 120 mg/kg, DHA-HCPT produced an ILS of 323% with three cures (Table 5). In contrast, PP-HCPT only produced an ILS of 123% with no cure at a dose of 150 mg/kg. Once again, the therapeutic efficacy of DHA-HCPT is higher than that of PP-HCPT. The ILS produced by cyclophosphamide was 173%.

Example 9
Anticancer Activity in the Lewis Tumor Model

When the drug was given one dose, i.p. DHA-HCPT showed significant activity in the Lewis lung carcinoma mouse model (Table 6). For example, at a dose of 120 mg/kg, it inhibited tumor growth by 83% while the bodyweight loss was only 10%. The parent HCPT inhibited tumor growth by 57% at a dose of 20 mg/kg with a 24% weight loss. The group treated with DHA-HCPT also lived longer.

In the multiple doses experiment (days 1, 5, and 9), at a dose of 120 mg/kg, DHA-HCPT produced 50% cures with minimum toxicity (Table 7). At a dose of 100 mg/kg, the tumor growth inhibition (TGI) is 88%. In contrast, cisplatin, one of the most effective drugs for treating lung cancer, produced a TGI of 73% at a very toxic dose of 5 mg/kg. These results demonstrate that the therapeutic index of DHA-HCPT is significantly higher than that of cisplatin.

Example 10
Anticancer Activity in the Colon 38 Carcinoma Tumor Model

When the drug was given once, at a dose of 120 mg/kg, DHA-HCPT significantly inhibited the tumor growth with a TGI of 91% (Table 8). In contrast, cisplatin produced a TGI of 88%. However, DHA-HCPT (weight loss of 16%) is less toxic than cisplatin (weight loss of 20%).

Two multiple dose experiments (days 1, 5, and 9) were preformed. The first experiment was designed to evaluate the antitumor activity of the drugs against early tumor, i.e., the tumors were transplanted on day 0, and the drugs were given beginning the next day. The second experiment was designed to evaluate the drug's activity against the established tumor, i.e., the tumors were transplanted on day 0, and the drugs were given when the tumors grew to 3–4 mm in size. In the early stage tumor model, at a dose of 100 mg/kg, DHA-HCPT significantly inhibited the tumor growth with a TGI of 78% (Table 9).

In the late tumor model, at a dose of 100 mg/kg, DHA-HCPT inhibited tumor growth by 80% (Table 10). These data suggest that DHA-HCPT is equally effective in both the early and late stage models.

TABLE 1

Curability of Cancers with Chemotherapy

A. Advanced cancers with possible cure

| | |
|---|---|
| Acute lymphoid and acute myeloid leukemia (pediatric/adult) | Gestational trophoblastic neoplasia Pediatric neoplasms |
| Hodgkin's disease (pediatric/adult) | Wilm's tumor |
| Lymphomas -certain types (pediatric/adult) | Embryonal rhabdomyocarcinoma Ewing's sarcoma |
| Germ cell neoplasms | Peripheral neuroepithelioma |
| Embryonal carcinoma | Neuroblastoma |
| Teratocarcinoma | Small cell lung carcinoma |
| Seminoma or dysgerminoma | Ovarian carcinoma |
| Choriocarcinoma | |

B. Advanced cancers possibly cured by chemotherapy and radiation

| | |
|---|---|
| Squamous carcinoma (head and neck) | Carcinoma of the uterine cervix |
| Squamous carcinoma (anus) | Non-small cell lung carcinoma (stage III) |
| Breast carcinoma | Small cell lung carcinoma |

C. Cancers possibly cured with chemotherapy as adjuvant to surgery

| | |
|---|---|
| Breast carcinoma | Osteogenic sarcoma |
| Colorectal carcinoma[a] | Soft tissue sarcoma |

D. Cancers possibly cured with "high-dose" chemotherapy with stem cell support

| | |
|---|---|
| Relapsed leukemias, lymphoid and myeloid | Chronic myeloid leukemia Multiple myeloma |
| Relapsed lymphomas, Hodgkin's and non-Hodgkin's | |

E. Cancers responsive with useful palliation, but not cure, by chemotherapy

| | |
|---|---|
| Bladder carcinoma | Cervix carcinoma |
| Chronic myeloid leukemia | Endometrial carcinoma |
| Hairy cell leukemia | Soft tissue sarcoma |
| Chronic lymphocytic leukemia | Head and neck cancer |
| Lymphoma - certain types | Adrenocortical carcinoma |
| Multiple myeloma | Islet-cell neoplasms |
| Gastric carcinoma | Breast carcinoma |

F. Tumor poorly responsive in advanced stages to chemotherapy

| | |
|---|---|
| Pancreatic carcinoma | Colorectal carcinoma |
| Biliary-tract neoplasms | Non-small cell lung carcinoma |
| Renal carcinoma | Prostate carcinoma |
| Thyroid carcinoma | Melanoma |
| Carcinoma of the vulva | Hepatocellular carcinoma |

[a]Rectum also receives radiation therapy

TABLE 2

Commonly Used Cancer Chemotherapy Agents

| Drug | Examples of Usual Doses |
|---|---|
| Alkylators | |
| Cyclophosphamide | 400–2000 mg/m$^2$ IV |
| | 100 mg/m$^2$ PO qd |
| Mechlorethamine | 6 mg/m$^2$ IV day 1 and day 8 |
| Chlorambucil | 1–3 mg/m$^2$ qd PO |
| Melphalan | 8 mg/m$^2$ qd × 5, PO |
| BCNU | 200 mg/m$^2$ IV |
| | 150 mg/m$^2$ PO |
| CCNU | 100–300 mg/m$^2$ PO |
| Ifosfamide | 1.2 g/m$^2$ per day qd × 5 + MESNA |
| Procarbazine | 100 mg/m$^2$ per day qd × 14 |
| DTIC | 375 mg/m$^2$ IV day 1 Nausea Flulike |
| Hexamethylmelamine | 260 mg/m$^2$ per day qd × 14–21 as 4 divided oral doses |
| Cisplatin | 20 mg/m$^2$ qd × 5 IV 1 q3–4 weeks or 100–200 mg/m$^2$/dose IV q3–4 weeks |
| Carboplatin | 365 mg/m$^2$ IV q3–4 weeks as adjusted for CrCl |
| Antitumor antibiotics | |
| Bleomycin | 15–25 mg/d qd × 5 IV bolus or continuous IV |
| Actinomycin D | 10–15 μg/kg per day qd × 5 IV bolus |
| Mithramycin | 15–20 μg/kg qd × 4–7 (hypercalcemia) or 50 μg/kg qod × 3–8 (antineoplastic) |
| Mitomycin C | 100 mg/m$^2$ q6 weeks |
| Etoposide (VP16–213) | 100–150 mg/m$^2$ IV qd × 3–5d or 50 mg/m$^2$ PO qd × 21d or up to 1500 mg/m$^2$/of dose (high dose with stem cell support) |
| Teniposide (VM–26) | 150–200 mg/m$^2$ twice per week for 4 weeks |
| Amsacrine | 100–150 mg/m$^2$ IV qd × 5 |
| Topotecan | 20 mg/m$^2$ IV q3–4 weeks over 30 min or 1.5–3 mg/m$^2$ q3–4 weeks over 24 h or 0.5 mg/m$^2$ per day over 21 days |
| Irinotecan (CPT II) | 100–150 mg/m$^2$ IV over 90 min q3–4 weeks or 30 mg/m$^2$ per day over 120 h |
| Doxorubicin and daunorubicin | 45–60 mg/m$^2$ dose q3–4 weeks or 10–30 mg/m$^2$ dose q week or continuous-infusion regimen |
| Idarubicin | 10–15 mg/m$^2$ IV q 3 weeks or 10 mg/m$^2$ IV qd × 3 |
| Epirubicin | 150 mg/m$^2$ IV q3 weeks |
| Mitoxantrone | 12 mg/m$^2$ qd × 3 or 12–14 mg/m$^2$ q3 weeks |
| Antimetabolites | |
| Deoxycoformycin | 4 mg/m$^2$ IV every other week |
| 6-Mercaptopurine | 75 mg/m$^2$ PO or up 500 mg/m$^2$ PO (high dose) |
| 6-Thioguanine | 2–3 mg/kg per day for up to 3–4 weeks |
| Azathioprine | 1–5 mg/kg per day |
| 2-Chlorodeoxyadenosine | 0.09 mg/kg per day qd × 7 as continuous infusion |
| Hydroxyurea | 20–50 mg/kg (lean body weight) PO qd or 1–3 g/d |
| Methotrexate | 15–30 mg PO or IM qd × 3–5 or 30 mg IV days 1 and 8 or 1.5–12 g/m$^2$ per day (with leucovorin) |
| 5-Fluorouracil | 375 mg/m$^2$ IV qd × 5 or 600 mg/m$^2$ IV days 1 and 8 |
| Cytosine arabinoside | 100 mg/m$^2$ per day qd × 7 by continuous infusion or 1–3 g/m$^2$ dose IV bolus |
| Azacytidine | 750 mg/m$^2$ per week or 150–200 mg/m$^2$ per day × 5–10 (bolus) or (continuous IV) |
| Gemcitabine | 1000 mg/m$^2$ IV weekly × 7 |
| Fludarabine phosphate | 25 mg/m$^2$ IV qd × 5 |
| Asparaginase | 25,000 IU/m$^2$ q3–4 weeks or 6000 IU/m$^2$ per day qod for 3–4 weeks or 1000–2000 IU/m$^2$ for 10–20 days |
| Antimitotic agents | |
| Vincristine | 1–1.4 mg/m$^2$ per week |
| Vinblastine | 6–8 mg/m$^2$ per week |
| Vinorelbine | 15–30 mg/m$^2$ per week |
| Paclitaxel | 135–175 mg/m$^2$ per 24-h infusion or 175 mg/m$^2$ per 3-h infusion or 140 mg/m$^2$ per 96-h infusion or 250 mg/m$^2$ per 24-h infusion plus G-CSF |
| Docetaxel | 100 mg/m$^2$ per 1-h infusion q3 weeks |
| Estramustine phosphate | 14 mg/kg per day in 3–4 divided doses with water >2 h after meals; Avoid Ca$^{2+}$-rich foods |

TABLE 3

Antitumor activity against L1210 leukemia in vitro*

| Drug | IC$_{50}$ ($\mu$M) |
|---|---|
| HCPT | 0.23 ± 0.03 |
| DRA-HCPT | 1.8 ± 1.5 |
| PP-HCPT | 30 ± 0.6 |
| Dox | 0.18 ± 0.09 |

*Cytotoxicity was measured in a 48-h proliferation assay. The results were reported as the minimal drug concentration that inhibits uptake of $^3$H-thymidine by 50%, and were the mean values of three experiments.

TABLE 4

Antitumor activity against L1210 leukemia in mice*

| Drug | Dose (mg/kg) | % Weight change[a] | % ILS | 30-day survivors |
|---|---|---|---|---|
| HCPT | 20 | −16 | 108 | 0 |
|  | 15 | −10 | 77 | 0 |
| DHA-HCPT | 180 | −12 | 154 | 2 |
|  | 60 | 1 | 138 | 0 |
|  | 40 | 2 | 108 | 0 |
| PP-HCPT | 73 | 2 | 77 | 0 |
|  | 37 | 5 | 46 | 0 |
| Cyclophosphamide | 200 | −9 | 123 | 0 |

*Male BDF$_1$ mice (6/group) were injected i.p. with 10$^5$ cells on day 0.
Drugs were administered i.p. on day 1.
[a]Group bodyweight change was between days 0 and the day at which time the group of mice had the lightest weight.
The median number of days of survival of the untreated mice was 6.5.

TABLE 5

Antitumor activity against L1210 leukemia in mice*

| Drug | Dose (mg/kg) | % Weight change[a] | % ILS | 30-day survivors |
|---|---|---|---|---|
| DHA-HCPT | 120 | −12 | 323 | 3 |
| PP-HCPT | 150 | −18 | 123 | 0 |
| Cyclophosphamide | 125 | −15 | 173 | 0 |

*Male BDF$_1$ mice (6/group) were injected i.p. with 10$^5$ cells on day 0.
Drugs were administered i.p. on days 1, 5 and 9.
[a]Group bodyweight change was between days 0 and the day at which time the group of mice had the lightest weight.

TABLE 6

Antitumor activity against Lewis lung carcinoma in mice*

| Drug | Dose (mg/kg) | % Weight change[a] | Tumor weight (g ± SD) | % TGI | % ILS | P value[b] |
|---|---|---|---|---|---|---|
| Control | — | — | 1.77 ± 0.89 | — | — | — |
| HCPT | 20 | −24 | 0.76 ± 0.59 | 57 | 16 | <0.01 |
| DHA-HCPT | 120 | −10 | 0.31 ± 0.18 | 83 | 33 | <0.01 |
|  | 80 | −5 | 0.93 ± 0.53 | 48 | 23 | <0.01 |

*Male BDF$_1$ mice (8/group) were injected s.c. with 10$^6$ cells on day 0.
Drugs were administered i.p. on day 1.
[a]Group bodyweight change was between days 0 and the day at which time the group of mice had the lightest weight.
[b]Compared to the control.

TABLE 7

Antitumor activity against Lewis lung carcinoma in mice*

| Drug | Dose (mg/kg) | % Weight change[a] | Tumor weight (g ± SD) | % TGI | P value[b] |
|---|---|---|---|---|---|
| Control | — | — | 1.20 ± 0.61 | — | — |
| DHA-HCPT | 100 | −9 | 0.15 ± 0.10 | 88 | <0.01 |
| Cisplatin | 5 | −19 | 0.32 ± 0.17 | 73 | <0.01 |

*Male BDF$_1$ mice (8/group) were injected s.c. with 10$^6$ cells on day 0.
Drugs were administered i.p. on days 1, 5, and 9.
[a]Group bodyweight change was between days 0 and the day at which time the group of mice had the lightest weight.
[b]Compared to the control.

TABLE 8

Antitumor activity against colon 38 carcinoma in mice*

| Drug | Dose (mg/kg) | % Weight change[a] | Tumor weight (g ± SD) | % TGI | P value[b] |
|---|---|---|---|---|---|
| Control | — | — | 1.20 ± 0.84 | — | — |
| Cisplatin | 10 | −20 | 0.14 ± 0.07 | 88 | <0.01 |
| DHA-HCPT | 120 | −16 | 0.11 ± 0.09 | 91 | <0.01 |

*Male BDF$_1$ mice (8/group) were injected s.c. with 10$^6$ cells on day 0.
Drugs were administered i.p. on day 1.
[a]Group bodyweight change was between days 0 and the day at which time the group of mice had the lightest weight.
[b]Compared to the control.

TABLE 9

Antitumor activity against early stage colon 38 carcinoma in mice*

| Drug | Dose (mg/kg) | % Weight change[a] | Tumor weight (g ± SD) | % TGI | P value[b] |
|---|---|---|---|---|---|
| Control | — | — | 1.13 ± 0.39 | — | — |
| DHA-HCPT | 150[c] | — | 0.18 ± 0.12 | 84 | <0.01 |
|  | 100 | −12 | 0.25 ± 0.22 | 78 | <0.01 |
|  | 67 | −10 | 0.64 ± 0.50 | 43 | <0.01 |

*Male BDF$_1$ mice (8/group) were injected s.c. with 10$^6$ cells on day 0.
Drugs were administered i.p. on days 1, 5 and 9.
[a]Group bodyweight change was between days 0 and the day at which time the group of mice had the lightest weight.
[b]Compared to the control.
[c]Drugs were given on days 1 and 5, and 4 mice died of toxicity.

TABLE 10

Antitumor activity against late stage colon 38 carcinoma in mice*

| Drug | Dose (mg/kg) | % Weight change[a] | Tumor weight (g ± SD) | % TGI | P value[b] |
|---|---|---|---|---|---|
| Control | — | — | 1.13 ± 0.39 | — | — |
| DHA-HCPT | 150c | — | 0.24 ± 0.18 | 79 | <0.01 |
|  | 100 | −14 | 0.22 ± 0.14 | 80 | <0.01 |

*Male BDF$_1$ mice (8/group) were injected s.c. with 10$^6$ cells on day 0.
Drugs administered i.p. on days 9, 13 and 17.
[a]Group bodyweight change was between days 0 and the day at which time the group of mice had the lightest weight.
[b]Compared to the control.
[c]Drugs were given on days 9 and 13, and 3 mice died of toxicity.

EQUIVALENTS

From the foregoing detailed description of the specific embodiments of the invention, it should be apparent that unique compositions and a unique procedure to produce fatty acid derivatives of campothecin have been described resulting in the synthesis of therapeutic compounds effective against mammalian cell proliferative diseases, e.g., cancer. Although particular embodiments have been disclosed herein in detail, this has been done by way of example for purposes of illustration only, and is not intended to be limiting with respect to the scope of the appended claims that follows. In particular, it is contemplated by the inventor that substitutions, alterations, and modifications may be made to the invention without departing from the spirit and scope of the invention as defined by the claims. For instance, the choice of fatty acid, or linker molecule, or the choice of doses, or the choice of route of administration of the compositions of the present invention is believed to be matter of routine for a person of ordinary skill in the art with knowledge of the embodiments described herein.

We claim:

1. A compound of the following formula or a pharmaceutically acceptable salt thereof:

Long chain unsaturated fatty acid-linker-CPT    (Formula I)

wherein:
the Long-chain unsaturated fatty acid is $C_{12}$–$C_{22}$ mono or poly unsaturated fatty acids;
the linker is -(alkyl)$_m$-(aryl)$_n$-C(O)— or -(aryl)$_m$-(alkyl)$_n$-C(O)—; wherein: m and n are independently 0–3, and m+n≧1; and
CPT is a camptothecin compound with the following general structure (Formula II):

(Formula II)

wherein: $R_1$–$R_5$ are H, halo, OH, $NO_2$, $NH_2$, alkyl, O-alkyl, NH-alkyl, or N(alkyl)$_2$.

2. The compounds of claim 1, wherein the long-chain unsaturated fatty acid is selected from the group consisting of palmitoleic acid, oleic acid, linoleic acid, linolenic acid, arachidonic acid, eicosapentaenoic acid (EPA) and docosahexaenoic acid (DHA).

3. A compound of the following formula or a pharmaceutically acceptable salt thereof:

Long chain unsaturated fatty acid-linker-CPT    (Formula I)

wherein:
the Long-chain unsaturated fatty acid is selected from the group consisting of palmitoleic acid, oleic acid, linoleic acid, linolenic acid, arachidonic acid, eicosapentaenoic acid (EPA) and docosahexaenoic acid (DHA);

CPT is a camptothecin compound with the following general structure (Formula II):

(Formula II)

wherein: $R_1$–$R_5$ are H, halo, OH, $NO_2$, $NH_2$, alkyl, O-alkyl, NH-alkyl, or N(alkyl)$_2$; and wherein the linker is a structure with the following Formula (III) and their acid addition salts.

Formula III

4. The compounds of claim 3, wherein CPT is selected from the group consisting of camptothecin, 9-aminocamptothecin, 10-hydroxycamptothecin, 7-ethyl-10-hydroxy-camptothecin, 9-N,N-dimethylaminomethyl-10-hydroxycamptothecin, and their acid addition salts.

5. The compounds of claim 3, wherein the compound is

6. The compounds of claim 3, wherein the compound is

7. The compounds of claim 3, wherein the compound is

8. A pharmaceutical composition comprising the compound of claim 1 and a pharmaceutically acceptable carrier.

9. A pharmaceutical composition comprising the compound of claim 3 and a pharmaceutically acceptable carrier.

10. A method for treating cancer in a patient comprising administering to the patient a therapeutically effective amount of the compound of claim 1, wherein the cancer is selected from the group consisting of leukemia, lung cancer and colon cancer.

11. A method for treating cancer in a patient comprising administering to the patient a therapeutically effective amount of the compound of claim 3, wherein the cancer is selected from the group consisting of leukemia, lung cancer and colon cancer.

* * * * *